United States Patent [19]

Yamabe et al.

[11] Patent Number: 4,946,690

[45] Date of Patent: Aug. 7, 1990

[54] CURATIVE AND PREVENTIVE METHOD FOR AQUARIUM FISH

[75] Inventors: Akira Yamabe; Ryuichi Yoshida, both of Tokyo, Japan

[73] Assignee: Japan Pet Drugs Co., Ltd., Tokyo, Japan

[21] Appl. No.: 348,252

[22] Filed: Apr. 27, 1989

[51] Int. Cl.⁵ ............................................. A01N 25/00
[52] U.S. Cl. ..................................... 424/665; 424/661; 424/663
[58] Field of Search ................. 424/661, 663, 665, 680

[56] References Cited

U.S. PATENT DOCUMENTS

| | | | |
|---|---|---|---|
| 2,963,400 | 12/1960 | Ross | 119/3 |
| 4,073,888 | 2/1978 | Snyder | 424/661 |
| 4,296,103 | 10/1981 | Laso | 424/660 |
| 4,333,922 | 6/1982 | Herschler | 424/680 |
| 4,499,077 | 2/1985 | Stockel et al. | 424/661 |
| 4,507,285 | 3/1985 | Kühne | 424/661 |

OTHER PUBLICATIONS

Chemical Abstracts, vol. 110 (1989): 71111n.
Midorishafo, Culturing Fish Course, vol. 9, "Golden Fish", 10/20/73.
Kingyo (Golden Fish), published by Midorishobo, Culturing fishes course, vol. 9, Oct. 1973, pp. 161–163 (partial translation).

*Primary Examiner*—Douglas W. Robinson
*Assistant Examiner*—Kevin E. Weddington
*Attorney, Agent, or Firm*—Cushman, Darby & Cushman

[57] ABSTRACT

There is disclosed a method for curing icthyophthiriasis and the like of aquarium fish and preventing them from being infected with the disease. By the use of stabilized chlorine dioxide.

4 Claims, No Drawings

CURATIVE AND PREVENTIVE METHOD FOR AQUARIUM FISH

BACKGROUND OF THE INVENTION

1. FIELD OF THE INVENTION

This invention relates to a curative and preventive method for aquarium fish and more particularly it relates to a curative and preventive method for aquarium fish which is most suitable for cure and prevention of diseases caused, for example, by parasites, such as ichthyophthiriasis in aquarium fish, e.g., goldfish, carp, and tropical fish.

2. RELATED ART STATEMENT

As diseases of aquarium fish, there have heretofore been known ichthyophthiriasis, bacterial parasitic fugi disease, etc. which are caused by parasitism of parasites such as trichinae. For curing such diseases of aquarium fish, there have heretofore been generally used curative drugs using dye drugs comprising methylene blue as their main constituent.

Such curative drugs for aquarium fish which comprise the dye drug as their main constituent have been well known to be effective in curing, for example, the above-mentioned diseases caused by ciliate parasites, such as ichthyophthiriasis and Parasitic fungi disease, and bacterial.

Such conventional curative drugs for aquarium fish, however, are disadvantageous in that since they, as described above, contain dyes such as methylene blue, they change the color of water in a water tank for breeding aquarium fish to blue, to make it difficult to enjoy the aquarium fish in the water tank. In addition, methylene blue is poisonous not only to the above-mentioned parasites but also to water grasses bred in the water tank together with the aquarium fish and hence tends to enfeeble or wither the water grasses. Furthermore, since methylene blue is easily oxidized in water, the dissolved oxygen concentration in water is decreased. Therefore, when diseased fish are placed in water containing a high concentration of the conventional curative drug, they tend to suffer from oxygen starvation. Accordingly, it is desired to develop a curative and preventive drug or method for aquarium fish which does not color water in a water tank and is not poisonous to water grasses.

SUMMARY OF THE INVENTION

The present invention was made in consideration of these points and relates to a curative and preventive method for aquarium fish which neither colors water nor affects the water grasses when applied to the above water tank.

The curative and preventive method for aquarium fish comprises applying a drug comprising, as its main constituent, stabilized chlorine dioxide prepared by stabilizing chlorine dioxide with an alkaline aqueous solution to a place in which aquarium fish such as goldfish or colored carp having Ichthyophthirius multiliis parasitic thereon live, namely, a water tank, a fish pond or the like, and thereby curing and preventing ichthyophthiriasis.

The curative and preventive method for aquarium fish of this invention uses a drug comprising stabilized chlorine dioxide as its main constituent and hence is advantageous in that stabilized chlorine dioxide is colorless and hence dose not color water, and that it can be used at a low concentration, so that the purpose can be achieved without any adverse influence on the water grasses.

DETAILED DESCRIPTION OF PREFERRED EMBODIMENT

According to the method of the present invention, a drug comprising stabilized chlorine dioxide as its main constituent is used for curing and preventing diseases of aquarium fish.

Stabilized chlorine dioxide is prepared by stabilizing chlorine dioxide in an aqueous alkali solution and possesses improved shelf life and no explosibility. It is produced and on the market in liquid form or powder form. Stabilized chlorine dioxide in either form can be used in the present invention. It is used after being properly diluted with water so as to adjust the concentration of chlorine dioxide to 5 to 30 ppm.

In the method of the present invention, ichthyophthiriasis of aquarium fish, in particular, high-class goldfish and colored carp, can be cured and prevented by adding such stabilized chlorine dioxide to water in a water tank at a concentration of 5 to 30 ppm. When the amount of stabilized chlorine dioxide added to a water tank is less than 5 ppm, the parasite is not annihilated. When it is 15 to 30 ppm, a sufficient effect can be obtained. When it exceeds 30 ppm, the curative effect hits the ceiling. As described below in the experimental examples, when it is about 15-30 ppm, the toxicity of stabilized chlorine dioxide is negligible, so that stabilized chlorine dioxide produces neither undesirable side effect on the aquarium fish nor adverse influence on water grasses in the water tank.

The method of the present invention is illustrated with the following experimental examples.

EXPERIMENTAL EXAMPLE 1

There were prepared a predetermined number of water tanks containing artificial fresh water (pH 7.0) obtained by adding calcium chloride, potassium sulfate, magnesium sulfate and sodium hydrogencarbonate to fresh water. A water grass (hornwort) was placed in each water tank and then ten *Oryzias latipes* were placed therein.

After being diluted, a stabilized chlorine dioxide liquid medicine (20000 ppm) was placed in the water tank to adjust the stabilized chlorine dioxide concentration to a predetermined value. The numbers of deaths $LC_{50}$ (median lethal concentration) after 24 hours and 48 hours of *Oryzias latipes* were calculated. Consequently, $LC_{50}$ after 24 hours and $LC_{50}$ after 48 hours are as high as 12500 ppm and 6100 ppm, respectively. Thus, it was found that at a low concentration of 30 ppm or less, stabilized chlorine dioxide had no adverse influence on the aquarium fish and the water grass.

Next, there were prepared five water tanks each containing 25 liters of water. In each water tank were placed 15 goldfish having Ichthyophthirius multiliis parasitic thereon, 15 healthy goldfish, and a water grass (hornwort). Stabilized chlorine dioxide was placed in four of the water tanks at concentrations of 30 ppm, 15 ppm, 5 ppm and 3 ppm, respectively. No drug was added to the remaining one water tank and this water tank was used as a control water tank.

Water in the water tanks containing stabilized chlorine dioxide was not colored at all. Seven days after the beginning of the test, no abnormality was observed in the water grass in these water tanks. We conjecture that this is because a very low concentration of stabilized chlorine dioxide was used.

The curative and preventive effects on the diseased fish were as shown in Table 1. That is, in the water tanks containing stable chlorine dioxide at concentrations of 30 ppm, 15 ppm and 5 ppm, respectively, Ichthyophthirius multiliis began to leave the fish die about 2 days after the beginning of test. Seven days after the beginning of test, most of the fish were completely cured of the disease. Only one of the healthy fish was infected with the disease in the water tank containing 5 ppm of stabilized chlorine dioxide, indicating that stabilized chlorine dioxide prevents infection of ichthyophthiriasis. The healthy goldfish showed no abnormality in action, namely, no adverse influence of chlorine dioxide was observed. On the other hand, in the case of ten of the 15 diseased fish in the control water tank, the condition of the disease became worse than before the beginning of test. That is, the number of Ichthyophthirius multiliis parasitic on the ten diseased fish was increased. Ichthyophthirius multiliis was parasitic on all the healthy fish in the control water tank. In the water tank containing 3 ppm of stabilized chlorine dioxide, neither sufficient curative effect nor sufficient preventive effect was brought about.

Thus, it was found that ichthyophthiriasis of the aquarium fish can be cured or prevented by placing stabilized chlorine dioxide in a water tank at a concentration of 5 to 30 ppm. From the fact that the effect of stabilized chlorine dioxide at a concentration of 15 ppm is not substantially different from that at a concentration of 30 ppm, it seems that when stabilized chlorine dioxide is practically used for curing and preventing the disease, its suitable concentration is 15 ppm.

TABLE 1

The results of ichthyophthiriasis curing test and inmate infection test (observation 7 days after the beginning of test)

| Item | Stabilized chlorine dioxide | 30 ppm | 15 ppm | 5 ppm | 3 ppm | Control water tank (0 ppm) |
|---|---|---|---|---|---|---|
| Condition of diseased fish | Cured | 13 fish | 12 fish | 9 fish | 4 fish | 0 |
| | Alleviated | 1 fish | 3 fish | 3 fish | 1 fish | 0 |
| | The same as before treatment | 1 fish | 0 | 3 fish | 6 fish | 3 fish |
| | Serious | 0 | 0 | 0 | 3 fish | 10 fish |
| | Died | 0 | 0 | 0 | 1 fish | 2 fish |
| The number of fish injected with ichthyophthiriasis among 15 healthy fish | | 0 fish | 0 fish | 1 fish | 7 fish | 15 fish |

Water temperature: 17–14° C.
Diseased fish tested: Red and white fan tail weighing 9 to 11 g (spotted with red and white colors).
Healthy fish tested: Fan tail weighing 9 to 11 g (patterned with only red color)

*The purpose of chosing the different species as diseased fish and healthy fish, respectively, is to distingush between them easily by the colors of their body surface.

As described above, the curative method for aquarium fish of the present invention is advantageous in that it makes it possible to cure diseases of aquarium fish without coloring water in a water tank for the aquarium fish and without producing an adverse influence on the aquarium fish and water grasses. Therefore, said method permits easy enjoyment of aquarium fish under medical treatment.

What is claimed is:

1. A curative and preventive method for aquarium fish which comprises applying stabilized chloride dioxide to a place line containing aquarium fish infected with ichthyophthiriasis, and thereby curing said aquarium fish and preventing healthy aquarium fish from being infected with, ichthyophthiriasis at the same time.

2. A method according to claim 1, wherein the aquarium fish are at least one goldfish.

3. A method according to claim 1, wherein the place which contains the aquarium fish is a water tank.

4. A method according to claim 1, wherein stabilized chloride dioxide is applied in a concentration of 5 to 30 ppm to the place which contains said aquarium fish.

* * * * *